United States Patent
Sandmann et al.

(10) Patent No.: US 8,987,672 B2
(45) Date of Patent: Mar. 24, 2015

(54) APPARATUS, SYSTEM AND METHOD FOR READING OUT X-RAY INFORMATION STORED IN STORAGE PHOSPHOR PLATES

(75) Inventors: Patrick Sandmann, Munich (DE); Anton Pirmann, Munich (DE); Günther Schindlbeck, Munich (DE); Johannes Hölzl, Grasbrunn (DE); Sven Behr, Munich (DE)

(73) Assignee: Agfa Healthcare NV, Mortsel (BE)

( * ) Notice: Subject to any disclaimer, the term of this patent is extended or adjusted under 35 U.S.C. 154(b) by 0 days.

(21) Appl. No.: 14/342,846

(22) PCT Filed: Aug. 13, 2012

(86) PCT No.: PCT/EP2012/003453
§ 371 (c)(1), (2), (4) Date: Mar. 5, 2014

(87) PCT Pub. No.: WO2013/034241
PCT Pub. Date: Mar. 14, 2013

(65) Prior Publication Data
US 2014/0203179 A1     Jul. 24, 2014

(30) Foreign Application Priority Data
Sep. 6, 2011 (EP) .................... 11007233

(51) Int. Cl.
*G01T 1/20* (2006.01)
*G01N 23/04* (2006.01)
*G03B 42/04* (2006.01)

(52) U.S. Cl.
CPC .............. *G01N 23/04* (2013.01); *G03B 42/045* (2013.01)
USPC ........................................................ 250/362

(58) Field of Classification Search
USPC ............................ 206/455; 250/362; 378/182
See application file for complete search history.

(56) References Cited

U.S. PATENT DOCUMENTS

| | | | |
|---|---|---|---|
| 3,409,149 A | | 11/1968 | Graux |
| 4,283,847 A | * | 8/1981 | May ................. 29/832 |
| 4,495,634 A | | 1/1985 | Suzuki |
| 4,889,233 A | * | 12/1989 | Torii ............... 206/455 |
| 4,973,134 A | * | 11/1990 | Finkenzeller et al. ........ 250/584 |

(Continued)

OTHER PUBLICATIONS

English translation of Official Communication issued in corresponding International Application PCT/EP2012/003453, mailed on Mar. 20, 2014.

(Continued)

*Primary Examiner* — David J Makiya
*Assistant Examiner* — Taeho Jo
(74) *Attorney, Agent, or Firm* — Keating & Bennett, LLP

(57) ABSTRACT

An apparatus and a corresponding system and method for reading out X-ray information stored in a storage phosphor plate includes a receiving device, in particular a cassette, for receiving the storage phosphor plate, a removal device for removing the storage phosphor plate from the receiving device, and a reading device for irradiating the storage phosphor plate removed from the receiving device with stimulation light and for detecting emitted light excited thereby in the storage phosphor plate. In order to permit as reliable a removal and/or return of the storage phosphor plate from and to the receiving device as possible while providing a simple design, the removal device has at least one removal element, which can be coupled to the storage phosphor plate and which can move along a curved path.

17 Claims, 5 Drawing Sheets

(56) References Cited

U.S. PATENT DOCUMENTS

| | | | |
|---|---|---|---|
| 4,984,780 A * | 1/1991 | Saito et al. | 271/292 |
| 5,065,866 A * | 11/1991 | Boutet et al. | 206/455 |
| 5,210,416 A | 5/1993 | Seto et al. | |
| 5,265,865 A | 11/1993 | Agano et al. | |
| 5,441,251 A | 8/1995 | Ohta | |
| 6,068,439 A | 5/2000 | Ohta | |
| 8,106,373 B2 * | 1/2012 | Holzl et al. | 250/580 |
| 2006/0091336 A1 * | 5/2006 | Muller et al. | 250/584 |
| 2011/0198254 A1 * | 8/2011 | Pirmann | 206/455 |

OTHER PUBLICATIONS

Official Communication issued in International Patent Application No. PCT/EP2012/003453, mailed on Oct. 5, 2012.

\* cited by examiner

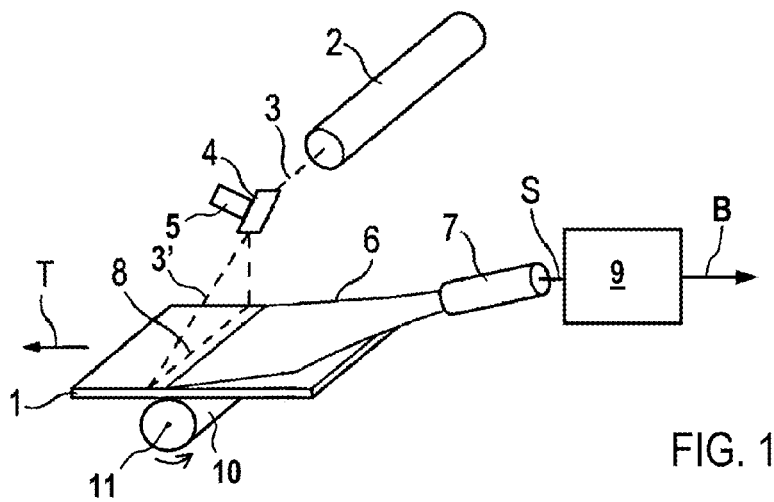
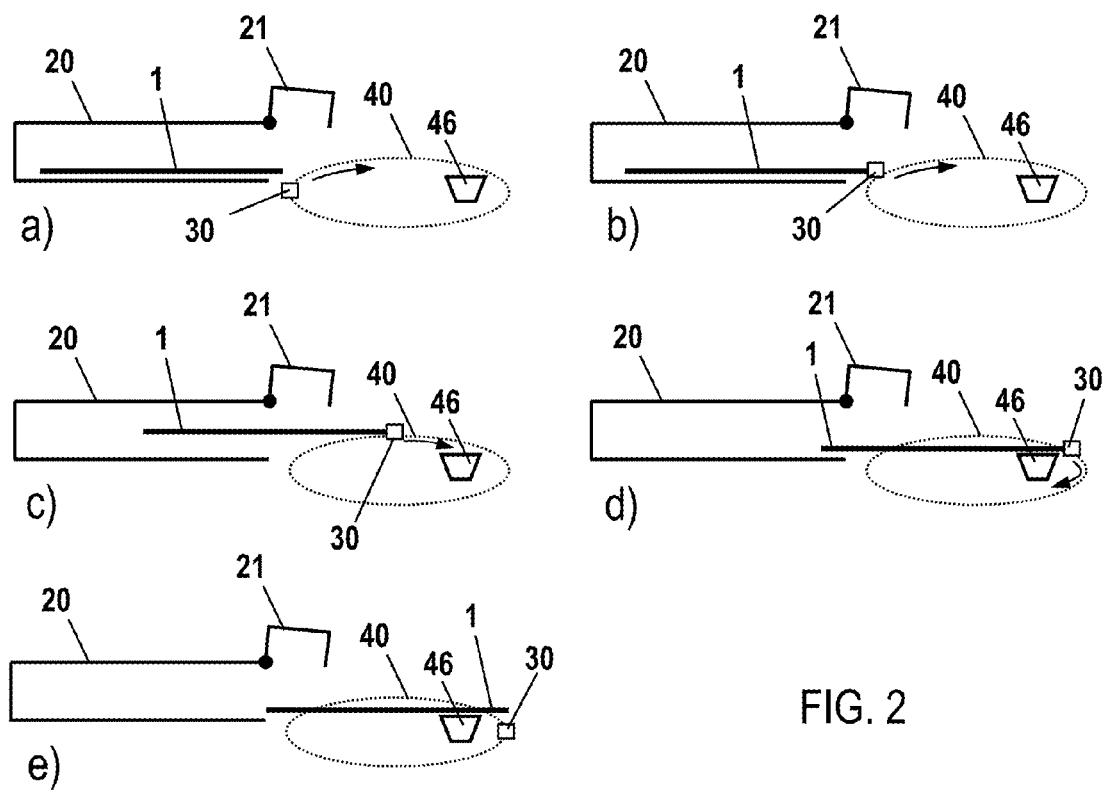
FIG. 1
FIG. 2

APPARATUS, SYSTEM AND METHOD FOR READING OUT X-RAY INFORMATION STORED IN STORAGE PHOSPHOR PLATES

CROSS-REFERENCE TO RELATED APPLICATIONS

This application is a 371 National Stage Application of PCT/EP2012/003453, filed Aug. 13, 2012. This application claims the benefit of European Application No. 11007233.7, filed Sep. 6, 2011, which is incorporated by reference herein in its entirety.

BACKGROUND OF THE INVENTION

1. Field of the Invention

The present invention relates to an apparatus, a system as well as a corresponding method for reading out X-ray information stored in storage phosphor plates.

2. Description of the Related Art

The storing of X-rays penetrating an object, for example a patient, as a latent image in a so-called storage phosphor plate constitutes an option for recording X-ray images. In order to read out the latent image, the storage phosphor plate is irradiated with stimulating light and thereby stimulated to emit emission light. The emission light, the intensity of which corresponds to the image stored in the storage phosphor plate, is detected by an optical detector and converted into electrical signals. The electrical signals are further processed, as required, and finally made available for analysis, in particular for medical-diagnostic purposes, by providing them on a corresponding output device, such as for example a monitor and/or a printer.

For prior art apparatuses and systems, provision is made of several mechanisms for removing the storage phosphor plate being in an initial position, in particular in a cassette, from the initial position or cassette, respectively, whereby, in particular in case of straightforward mechanisms, it is not possible to ensure also a reliable removal and/or return of the storage phosphor plate for all application cases.

SUMMARY OF THE INVENTION

The problem addressed by preferred embodiments of the present invention is to provide an apparatus, a system and a corresponding method for reading out storage phosphor plates that facilitate, with a straightforward configuration, a removal and/or return of the storage phosphor plate from and into, respectively, the initial position, in particular a cassette, that is as reliable as possible.

Preferred embodiments of the present invention provide an apparatus, a system and a method, respectively, as described below.

The apparatus according to a preferred embodiment of the present invention comprises a receiving device for receiving a storage phosphor plate being present, in particular, in a cassette, a removal device for removing the storage phosphor plate from the receiving device and a read-out device for irradiating the storage phosphor plate which has been removed from the receiving device with stimulating light and for detecting emission light which is thereby stimulated in the storage phosphor plate and is characterized in that the removal device comprises at least one removal element which can be coupled to the storage phosphor plate and which is moveable along a curved path.

The system according to a preferred embodiment of the present invention comprises a storage phosphor plate as well as the apparatus.

The method according to a preferred embodiment of the present invention comprises the following steps: removing a storage phosphor plate being present, in particular, in a cassette from a receiving device and reading out the storage phosphor plate which has been removed from the receiving device by irradiating it with stimulating light and detecting emission light which is thereby stimulated in the storage phosphor plate, whereby during the removal of the storage phosphor plate a removal element which moves along a curved path is coupled to the storage phosphor plate.

Preferred embodiments of the present invention are based on the thought of guiding the removal element along a curve, wherein the removal element couples automatically, at a certain position along the curve, to the storage phosphor plate that is located in an initial position, in particular in a cassette, and that the removal element moves the storage phosphor plate, during the further course along the curve, at least partially out of the initial position and is finally decoupled automatically at a further position on the curve from the storage phosphor plate.

The coupling and decoupling, respectively, of the removal element to and from, respectively, the storage phosphor plate takes hereby place, in contrast to known devices and methods, solely on the basis of the motion that is executed by the removal element itself along the curved path, meaning on the basis of the curve-like motion of the removal element itself, so that—aside from a device for generating the curve-like motion, such as for example one or more rollers, pulleys, belts or connecting rods—no further elements or mechanisms are required to effect a coupling or decoupling, respectively.

As a result, the removal element can be designed as a hook that, as a result of the curve-like motion thereof, moves toward the storage phosphor plate and engages a corresponding hooking engagement that is provided in the storage phosphor plate, and releases the hooking engagement again automatically on the basis of the curve-like motion thereof after the transport of the storage phosphor plate along a certain path length.

Preferred embodiments of the present invention become efficacious in a particularly advantageous manner when the coupling of the recording element and the storage phosphor plate occurs by forced closure, for example as a result of magnetic attraction forces. The removal element can, as an example, be designed as a magnet that, on the basis of the curve-like motion, moves initially toward the storage phosphor plate and is coupled to the, at least in sections, ferromagnetic storage phosphor plate by magnetic attraction forces. Due to its motion along a curved path the magnet will again move away from the storage phosphor plate, releasing itself in the process automatically from the storage phosphor plate, meaning the forced closure due to magnetic forces is broken off.

On the basis of the invention, as the described preferred embodiments illustrate, additional coupling and decoupling mechanisms, respectively, such as closing and opening gripper jaws, can be omitted during the coupling as well as also during the decoupling of the removal element to and from, respectively, the storage phosphor plate, without compromising the reliability of the removal and return, respectively, of the storage phosphor plate from and into, respectively, the cassette.

In summary it should therefore be noted that preferred embodiments of the invention facilitate, with a straightforward configuration, a reliable removal and/or return of the storage phosphor plate from and into the, respectively, initial position, in particular from and into, respectively, the cassette.

Preferably, the plane of the curved path of the removal element runs substantially vertical to the plane of the storage phosphor plate. This makes it possible by straightforward structure that the removal element moves toward the storage phosphor plate during the motion along a part of the curved path, and moves again away from the storage phosphor plate along a further part of the curved path, so that the removal element can automatically couple to the storage phosphor plate and decouple again from the storage phosphor plate.

In a further preferred embodiment, provision is made that at least one section of the curved path is substantially ellipse-shaped, in particular circular. Such paths can be implemented by particularly straightforward structure, for example by pulleys or rollers with circular cross-section or crank and/or eccentric drives, and feature simultaneously a shape that facilitates a secure coupling and decoupling of the removal element.

Furthermore preferred is that the removal element is disposed and/or designed in such a way that the removal element couples to the storage phosphor plate in a first position on the path, the storage phosphor plate that is coupled to the removal element is at least partially removed from the receiving device during a motion of the removal element from the first position to a second position on the path, and the storage phosphor plate that is coupled to the removal element is decoupled from the storage phosphor plate during a motion of the removal element beyond the second position on the path. This preferred embodiment permits that the removal element couples automatically to the storage phosphor plate during a, preferably continuous, motion of the removal element along a section of the curved path, conveys the storage phosphor plate at least partially out of the cassette, and finally decouples automatically again from the storage phosphor plate. The removal of the storage phosphor plate can thereby be implemented particularly straightforwardly, wherein reliability to a high degree is assured at the same time.

Preferably, the removal element features a magnetic element via which the removal element can be magnetically coupled to the storage phosphor plate.

Preferably, the storage phosphor plate is permanently magnetic and/or ferromagnetic in at least the area in which the removal element and the storage phosphor plate come into contact with each other, in particular in the edge region of the storage phosphor plate. This can be implemented, for example, by the storage phosphor plate having a base layer with a storage phosphor layer that is located thereon, wherein in the base layer one or more permanently magnetic and/or ferromagnetic areas are provided. In particular, the base layer has a permanently magnetic and/or ferromagnetic layer, for example a metal foil, which extends substantially across the entire area of the base layer. Using storage phosphor plates configured in this way assures, in the case of magnetically designed removal elements, a particularly high degree of reliability during the removal and return from and into, respectively, the cassette.

In a further preferred embodiment, provision is made that the removal element is disposed on a connecting rod. In particular, an elliptical or circular path of the removal element can be implemented in a particularly robust, straightforward and cost-effective way using a connecting rod.

In a further preferred development of the invention, the removal element is disposed on a rotatable pulley or roller. In particular, a circular path motion of the removal element is implemented in a straightforward, robust and cost-effective way also through the use of pulleys or rollers, respectively.

Alternatively or in addition, the removal element is disposed on a belt that is guided along at least one curved guide, in particular a rotatable pulley or roller. In so doing the particular advantage is achieved, in addition to the advantages already mentioned in the context of the use of pulleys and rollers, that the storage phosphor plate that is removed from the cassette can be supported at least partially by the upper side of the belt when being removed and additional provisions for the support of the storage phosphor plate can therefore be omitted.

In a further preferred embodiment of the invention, a transport device is provided for transporting the storage phosphor plate relative to the read-out device, wherein the removal device is designed for the conveyance of the removed storage phosphor plate toward the transport device and/or away from the transport device. For example, one or several rollers serve as transport device, the rollers transporting the storage phosphor plate past the deflected stimulating light beam of the read-out device. In this case, the removal device is designed such that the removal device transfers the storage phosphor plate to the transport device and is then decoupled from the storage phosphor plate. This has the advantage that the further transport of the storage phosphor plate past the read-out device cannot affected anymore by the removal device and possible vibrations or wow and flutter can no longer be passed on to the storage phosphor plate while the same is being read out.

Preferably, the transport device has a roller drive and at least one roller, which can be made to move rotationally by the roller drive and has at least one magnetic area. As a result, a storage phosphor plate, which has permanently magnetic and/or ferromagnetic areas, preferably in the base layer, can be transported by only one roller in a straightforward and reliable way. The use of just one magnetic roller instead of the conventionally used non-magnetic double rollers also has the advantage that a transfer of the storage phosphor plate from the removal device to the transport device is particularly straightforward and reliable due to the fact that the storage phosphor plate to be transferred is already being "picked up" by the magnetic roller due to magnetic attraction forces before it has reached the apex line of the roller—corresponding to the line of contact in the case of a double roller. Overall the removal and transfer of the storage phosphor plate is particularly secure as a result.

Furthermore preferred is that the removal device is designed for the conveyance of the removed storage phosphor plate into the interior of the apparatus. The storage phosphor plate is preferably located in a cassette that is inserted from the outside into a receiving device that is located on the housing of the apparatus. A partial section of the cassette protrudes after the insertion of the cassette into the interior of the housing of the apparatus. The cassette that is protruding into the interior of the housing is opened using a suitable opening mechanism, and the removal device that is disposed in the interior of the housing of the apparatus then conveys the storage phosphor plate that is located in the cassette into the interior of the apparatus. Preferably, the removal device is also designed for a return of the storage phosphor plate to the receiving device, in particular into the cassette.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 1 a schematic representation of an apparatus and a system, respectively, for reading out storage phosphor plates.

FIG. 2 a schematic representation of the removal of a storage phosphor plate from a cassette in a first preferred embodiment.

DETAILED DESCRIPTION OF THE PREFERRED EMBODIMENTS

Figure 3:
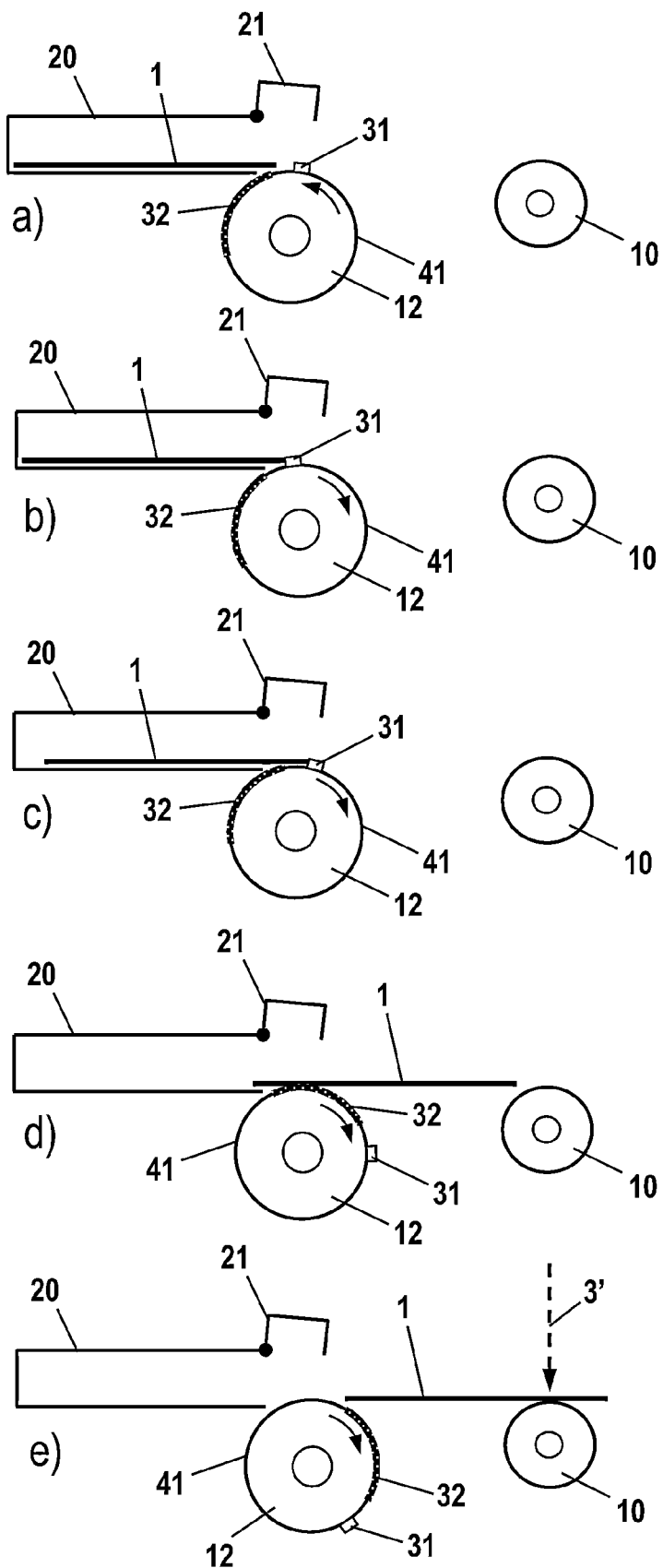
FIG. 3 a schematic representation of the removal of a storage phosphor plate from a cassette in a second preferred embodiment.

FIG. 1 shows a read-out device for reading out a storage phosphor plate 1. A laser 2 generates a stimulating light beam 3 that is deflected by a deflection element 4 in such a way that the stimulating light beam moves along a line 8 across the storage phosphor plate 1 to be read out. The deflection element 4 has a reflecting area, in particular in the form of a mirror, that is made to move oscillatingly by a drive device 5. Alternatively, the deflection element 4 can have a polygon mirror that is made to move rotationally by the drive device 5, in this case a motor, and deflects the stimulating light beam 3 across the storage phosphor plate 1.

During the movement of the deflected stimulating light beam 3' across the storage phosphor plate 1, the storage phosphor plate emits emission light depending on the X-ray information stored therein, which emission light is collected by an optical collection device 6, for example an optical fiber bundle or a suitable mirror device, and detected by an optical detector 7, preferably a photomultiplier (PMT), and is thereby converted into a corresponding detector signal S.

The detector signal S is supplied to a device 9 in which digital image signal values B for individual pixels of the read out X-ray image are derived.

The transport of the storage phosphor plate 1 in the transport direction T by a transport device has the effect that individual lines 8 of the storage phosphor plate 1 are successively read out, and a two-dimensional composite X-ray image is thereby obtained that is composed of individual pixels with respectively one associated image signal value B.

In the example shown, the transport device comprises a roller 10 which is put into rotation about rotational axis 11 by a roller drive (not shown). The storage phosphor plate 1 is supported on its underside by roller 10 and is conveyed by a rotation of the roller 10 in the direction T as a result of the frictional engagement that arises hereby.

The roller 10 in the displayed example has magnetic, preferably permanently magnetic or electromagnetic, elements or areas that interact with magnetic or ferromagnetic elements or areas that are provided on the storage phosphor plate 1, so that the storage phosphor plate 1 is attracted by the roller 10, which significantly reinforces the frictional engagement and thereby assures a particularly reliable transport of the storage phosphor plate 1.

The magnetic elements or areas can be applied to the cylinder-shaped surface of the roller 10, for example in the form of a coating or a casing of the surface with a magnetic layer or a magnetic band. Preferably, the roller 10 itself is permanently magnetic or ferromagnetic, so that the magnetic layer or the magnetic band, respectively, is already held securely on the roller 10 due to magnetic attraction forces.

The magnetic elements or areas can, alternatively or in addition, however also be provided in the interior of a roller 10 that is designed as a hollow body, for example through the arrangement on a carrier that is located in the interior of the roller 10. The hollow body of the roller 10 does not have to be magnetic or ferromagnetic in this case, but can also be para- or diamagnetic. Preferably, this is, in this case, a hollow body made of aluminum.

FIG. 2 shows a schematic representation of the removal of a storage phosphor plate 1 from a cassette 20 in a first preferred embodiment of the invention. On a face side of the cassette 20 is an opening, as can be recognized from the cross-sectional display selected here, which can be closed via a flap 21 that is disposed in the area of the face side. The storage phosphor plate 1 is preferably disposed and/or dimensioned in the cassette 20 in such a way that a front end of the storage phosphor plate 1 protrudes somewhat from the opening on the face side of the cassette 20 when the flap 21 is open. Alternatively, however, preference can be given to placing the front end of the storage phosphor plate 1, when the flap 21 of cassette 20 is open, approximately at the height of the opening of the cassette 20 or also just within the opening of the cassette 20.

In the phase of the removal process displayed in part a) of FIG. 2, a removal element 30, which is only rendered heavily schematized, is located just below the storage phosphor plate 1 that protrudes partially from the opening of the cassette 20. The removal element 30 preferably has one or several permanent magnets that can couple magnetically to the front end of the storage phosphor plate 1, which is permanently magnetic and/or ferromagnetic at least in the area of the front end.

Alternatively or in addition, the removal element 30 can have one or more grippers or hooks that engage or hook into, respectively, the front end of the storage phosphor plate 1.

According to a preferred embodiment of the invention, the removal element 30 is designed and/or disposed in a way that it is moved on an at least partially curved path 40 during the removal of the storage phosphor plate 1 from the cassette 20, thereby couples automatically to the storage phosphor plate 1 due to the executed path motion, and decouples automatically again from the storage phosphor plate. This is explained in more detail on the basis of parts b) to e) of FIG. 2.

In the phase displayed in part b) of FIG. 2, the removal element 30 has reached the height of the front end of the storage phosphor plate 1 and can couple to the storage phosphor plate magnetically and/or in a positive locking manner.

After continuing the motion along the curved path 40 (see delineated arrow), the phase displayed in part c) of FIG. 2 is reached, where the storage phosphor plate 1 is guided approximately halfway out of the cassette 20 by the removal element 30.

In the phase displayed in part d) of FIG. 2, the removal element 30 has been moved further along the curved path 40, so that the storage phosphor plate 1 is located already mostly outside the cassette 20. If the motion of the removal element 30 continues along the curved path 40 (see delineated arrow), the storage phosphor plate 1 comes into contact with a support element 46 that has, for example, a level plane that extends substantially parallel to the storage phosphor plate 1, so that the storage phosphor plate 1 can no longer follow the further path motion of the removal element 30. The magnetic coupling or positive locking, respectively, of the removal element 30 to the storage phosphor plate 1 is eliminated, "breaking it off" to a certain extent.

The phase in which the storage phosphor plate 1 has been removed completely from the cassette 20 and the removal element 30 has been decoupled from the storage phosphor plate 1 is displayed in part e) of FIG. 2.

The storage phosphor plate 1 that has been removed from the cassette 20 can now be transported past a read-out device by an additional transport device, for example a roller 10 (see FIG. 1), be read out there and be conveyed back into the position shown in part e) of FIG. 2 after the reading out. The return transport of the storage phosphor plate 1 by the removal element 30 back into the cassette 20 then takes place corresponding to the phases shown in parts a) to e) of FIG. 2, in the reverse order. The previous explanation regarding the respective figure sections apply correspondingly in each case.

In the case of the preferred embodiment shown in FIG. 2, the removal element 30 moves along a part of the ellipse-shaped path 40. In principle, the invention can also be executed by a motion of the removal element 30 along curved paths that have other shapes. This includes, for example, parabolic, hyperbolic or circular paths as well as sections of such paths.

The plane of the curved path 40 lies preferably vertically to the plane of the storage phosphor plate 1, but it can also be inclined at a finite angle relative to the plane of the storage phosphor plate 1.

FIG. 3 shows a schematic representation of the removal of a storage phosphor plate 1 from a cassette 20 in a second preferred embodiment of the invention. Regarding the cassette 20, including flap 21, the statements in the context of the preferred embodiment shown in FIG. 2 apply correspondingly.

A substantially circular wheel 12 is provided in the area of the opening of the cassette 20, in which circular wheel's circumferential area a first removal element 31 as well as a second removal element 32 are provided. The removal element 31 is preferably a permanent magnet or a gripper that can couple to the front end of the storage phosphor plate 1 by magnetic forces or in a positive locking way, respectively. Moreover, the statements in the context of the removal element 30 shown in FIG. 2 apply correspondingly to the removal element 31.

Preferably, the removal element 31 is elevated relative to the substantially circular circumferential area of the wheel 12. In contrast thereto, the second removal element 32 is elevated relative to the circular circumference of the wheel 12 to a lesser extent, or it is flush therewith. Furthermore, the second removal element 32 extends across a larger angular range of the circumference of the wheel 12 than is the case for the first removal element 31. The first removal element 31 is designed as a cuboid magnet, for example, while the second removal element 32 is designed as a plane area on the circumference of the wheel 12, for example in the shape of a magnetic layer applied to the circumference of the wheel 12.

A roller 10 is disposed at a certain distance to the wheel 12, by which roller the storage phosphor plate 1 which has been removed from the cassette 20 is transported past a read-out device (not shown, see FIG. 1).

In the phase displayed in part a) of FIG. 3, the wheel 12 is located in a rotating position in which neither the first nor the second removal element 31 and 32, respectively, are coupled to the storage phosphor plate 1.

In the phase displayed in part b) of FIG. 3, the wheel 12 is rotated slightly to the left, so that the first removal element 31 comes into contact with the front end of the storage phosphor plate 1 and is coupled to the storage phosphor plate 1 by magnetic attraction forces.

Subsequently, the wheel 12 is rotated into the opposite direction, wherein the first removal element 31 conveys the storage phosphor plate 1 that is coupled to the removal element out of the cassette 20 ((part c) of FIG. 3).

Through a continuation of the rotational motion of the wheel 12, the phase displayed in part d) of FIG. 3 is reached, after the magnetic coupling of the first removal element 31 with the storage phosphor plate 1 has been released automatically through "breaking off" (see the above statements in the context of the parts d) and e) of FIG. 2). In this phase, the second removal element 32 is now magnetically coupled to the storage phosphor plate 1, wherein the latter is then conveyed further in the direction of the roller 10 due to the rotational motion of the wheel 12.

In the case of a continuation of the rotational motion of the wheel 12, the second removal element 32 is finally also decoupled automatically from the storage phosphor plate 1, which meanwhile positions itself on the magnetic roller 10 (see statements regarding roller 10 in the context of with FIG. 1) and can be transported by the roller past the deflected stimulating light beam 3' of the read-out device.

After the storage phosphor plate 1 has been completely read out in the read-out device, the storage phosphor plate is conveyed again toward the wheel 12 by the roller 10 and can subsequently be conveyed back into the cassette 20, initially through coupling with the second removal element 32 as well as subsequently with the first removal element 31, corresponding to parts a) to e) in FIG. 3 in reversed order.

The motion of the removal elements 31 and 32 according to the invention along a curved path therefore takes place in the preferred embodiment displayed in FIG. 3 along a substantially circular path that is established by the circular circumference 41 of the wheel 12.

Figure 4:
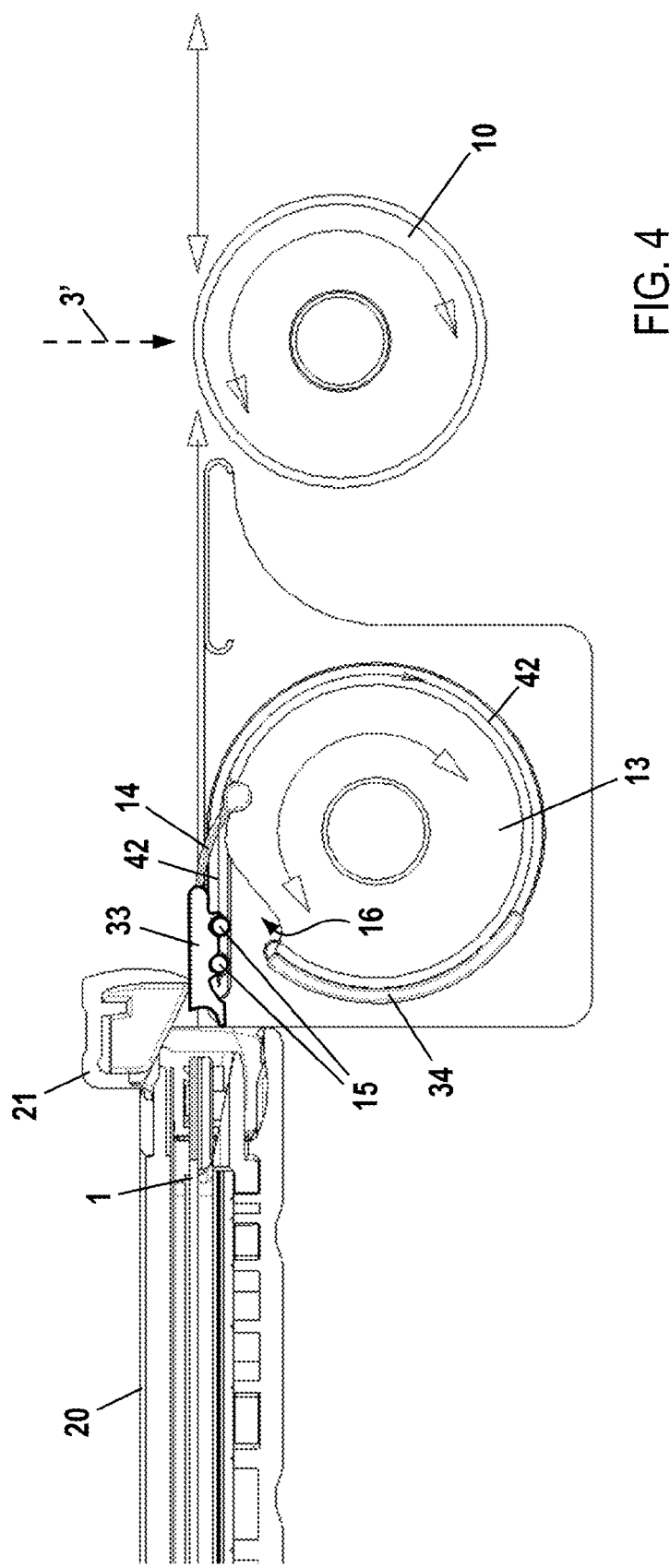
FIG. 4 a third preferred embodiment of the removal of a storage phosphor plate from a cassette.

FIG. 4 shows a third preferred embodiment of the invention that concerns substantially a development of the preferred embodiment shown in FIG. 3.

In this display also, the face side flap 21 of the cassette 20 is open. A first removal element 33 is attached via a coupling element 14 to a rotatably mounted and driven transport pulley 13. The coupling element 14 is designed, for example, as a latch or a strap that is connected with one end to the first removal element 33, and is attached, preferably pivotably mounted, at the other end in the area of the circumference of the transport pulley 13.

Magnets are preferably provided on the first removal element 33 and can be magnetically coupled to the front end of the storage phosphor plate 1 that is located in the cassette 20. The front end of the storage phosphor plate 1 is correspondingly designed to be permanently magnetic and/or ferromagnetic.

The first removal element 33 is guided along a slide track 42 during a rotation of the transport pulley 13, which slide track runs substantially circularly and transitions into a substantially straight course in the vicinity of the opening of the cassette 20. In this case, the first removal element 33 is preferably guided by slide pulleys 15 to assure a reliable guiding in the correct position.

The transport pulley 13 is furthermore provided with a second removal element 34, which preferably is a plane magnetic area to which the above statements regarding the second removal element 32, which is shown in FIG. 3, apply correspondingly.

For the removal of the storage phosphor plate 1 that is located in the cassette 20, the transport pulley 13 is rotated initially slightly to the left, so that the first removal element 33 is moved along the substantially straight section of the track 42 in the direction toward the front end of the storage phosphor plate 1, and couples to the end magnetically. Then, the rotational direction of the transport pulley 13 is reversed and the first removal element 33 pulls the storage phosphor plate 1 out of the cassette 20.

During the rotation of the transport pulley 13 to the right, the first removal element 33, which is mounted at the transport pulley 13 via the coupling element 14, is guided along the substantially circular section of track 42. To facilitate a decoupling of the removal element 33 from the storage phosphor plate 1 during a further rotation of the transport pulley 13, a recess 16 is provided in the transport pulley 13, in which recess the first removal element 33 can be at least partially received during the continued rotational motion of the transport pulley 13

After the automatic decoupling of the first removal element 33 from the storage phosphor plate 1, the latter is coupled to the transport pulley 13 via the second removal element 34 and transported further in the direction of the roller 10 during continued rotation until the plane- and/or segment-shaped second removal element 34 finally also decouples automatically from the storage phosphor plate 1 and "dives away" downward.

The storage phosphor plate 1 then rests, at least in the area of the front end thereof, on the roller 10 and can, as already explained in the context of FIG. 1, be read out in the read-out device through the detection of the emission light that is stimulated by a moving stimulating light beam 3'.

After the reading out of the storage phosphor plate 1, the storage phosphor plate 1 is moved again in the direction of the transport pulley 13 by the roller 10, and is then conveyed back into the cassette 20 by the transport pulley aided by the second and first removal element 34 and 33, respectively, as previously described but in reversed order. Moreover, the statements in the context of the preferred embodiment shown in FIG. 3 apply correspondingly for this preferred embodiment example.

As an alternative to the example described in detail previously, it is also possible that the track-guided first removal element 33 is not guided along the track 42 by the transport pulley 13, but that a separate drive is provided for that purpose. The motion of the first removal element 33 on the one hand as well as that of the second removal element 34 on the other hand takes therefore place separately in this alternative. Alternatively or in addition, it is also possible to actuate the transport pulley 13 using a drive that is also provided for actuating the roller 10, so that instead of respectively separate drives for the roller 10 and the transport pulley 13 only one drive is required.

Figure 5:
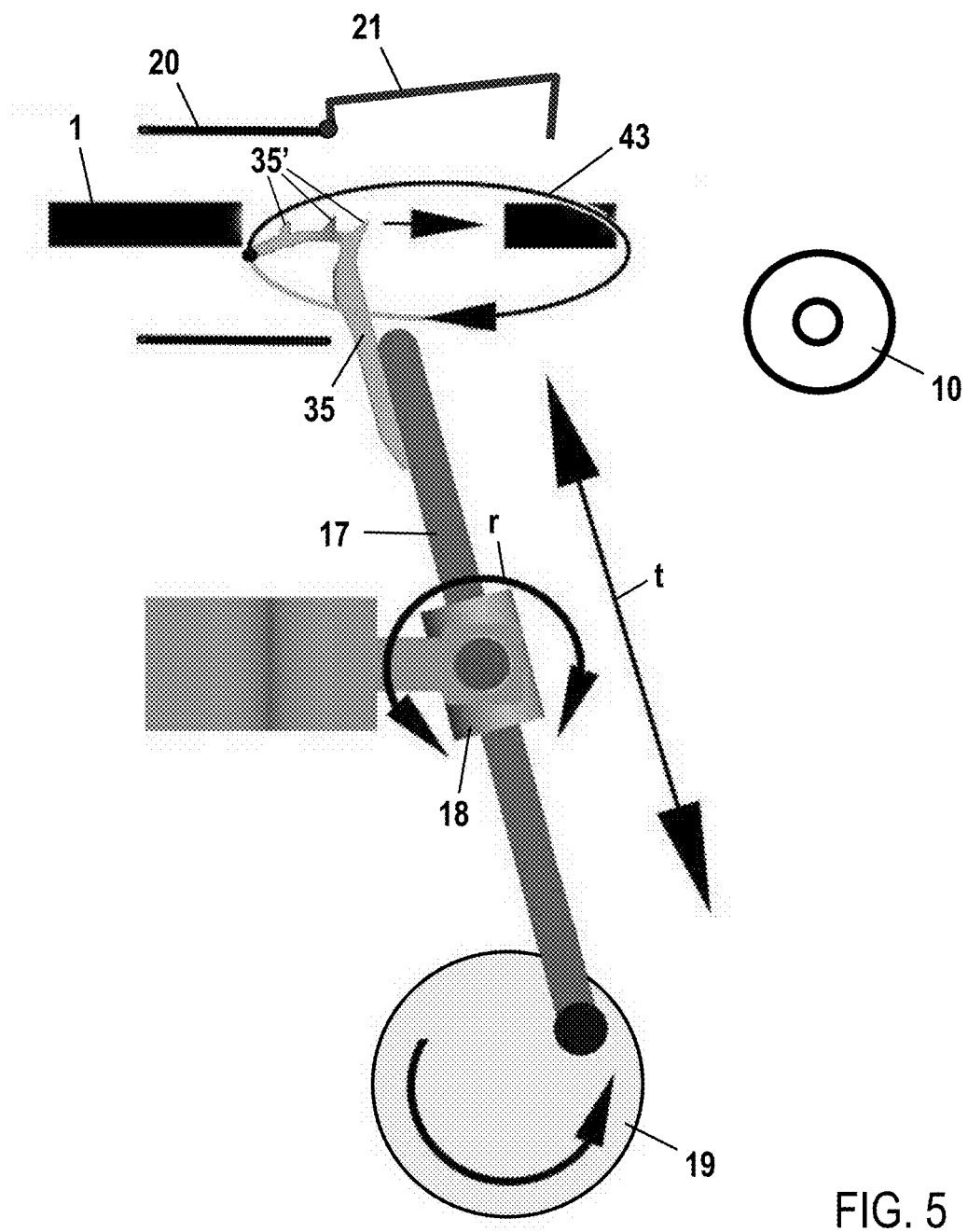
FIG. 5 a fourth preferred embodiment of the removal of a storage phosphor plate from a cassette.

FIG. 5 shows a fourth preferred embodiment of the invention for the removal of a storage phosphor plate 1 from a cassette 20 whose face side flap 21 is open. A hook-shaped element, which is attached to a connecting rod 17, is provided as the removal element 35 in the displayed example. The connecting rod 17 is supported in a displaceable manner in a rotatably mounted retaining sleeve 18 and is attached in an eccentrically rotatable manner to a rotating drive roller 19. As a result of a rotation of the drive roller 19, the connecting rod 17 is put into a translational motion in the direction t, as well as simultaneously into a rotational motion in the direction r.

As a result of the superposition of these motions, the removal element 35, which is located at the other end of the connecting rod 17, is moved along an ellipse-shaped path 43. In so doing, the removal element 35, which is designed hook-shaped and preferably has additional counter hooks 35' or roughed areas on the surface facing the underside of the storage phosphor plate 1, can come into contact with the underside of the front end of the storage phosphor plate 1, hook-in there or couple at least in a frictional engagement to the front end, so that during a continuation of the motion of the removal element 35 along the path 43 the storage phosphor plate 1 is conveyed out of the cassette 20 by its front end by the removal element 35 and transported in the direction of the roller 10 that is provided in the area of the read-out device, and is transferred to the roller.

As a result of the removal element 35 being guided along the ellipse-shaped path 43, the coupling, which is positive locking and/or frictionally engaged, between the removal element 35 on the one hand and the front end of the storage phosphor plate 1 on the other hand is released automatically when the removal element 35 is located on a side of the ellipse-shaped path 43 that is located opposite the position presently being displayed, and/or when the removal element is located beneath this position. A reversal of the rotational movement of the drive roller 19 can correspondingly couple the removal element 35 to the storage phosphor plate 1 in a positive locking and/or frictionally engaged manner, and convey the storage phosphor plate back in the direction of the cassette 20.

In the present example, a coupling between the hook-shaped removal element 35 and the front end of the storage phosphor plate 1 is positive locking, in particular due to the engagement of the hook, and/or frictionally engaging, in particular due to a contact between the upper side of the hook that is roughened or equipped with counter hooks 35', with the underside of the storage phosphor plate 1. Alternatively or in addition, it is however also possible to design the removal element 35 magnetically so that the removal element can be coupled alternatively or additionally, respectively, via magnetic forces to the storage phosphor plate 1, which is permanently magnetic and/or ferromagnetic at least in the area of the front end. Moreover, the foregoing statements, in particular in the context of the preferred embodiment shown in FIG. 2, apply correspondingly to this preferred embodiment.

In the preferred embodiment shown in FIG. 5, the curved path 43 is implemented using a so-called slider crank. Alternatively, it is however also possible to implement a curved path via cam disks, cam drives, eccentric drives, a belt drive disposed on a curved path or traverses that are designed curve-shaped, which can be followed using simple bearings in a track.

Figure 6:
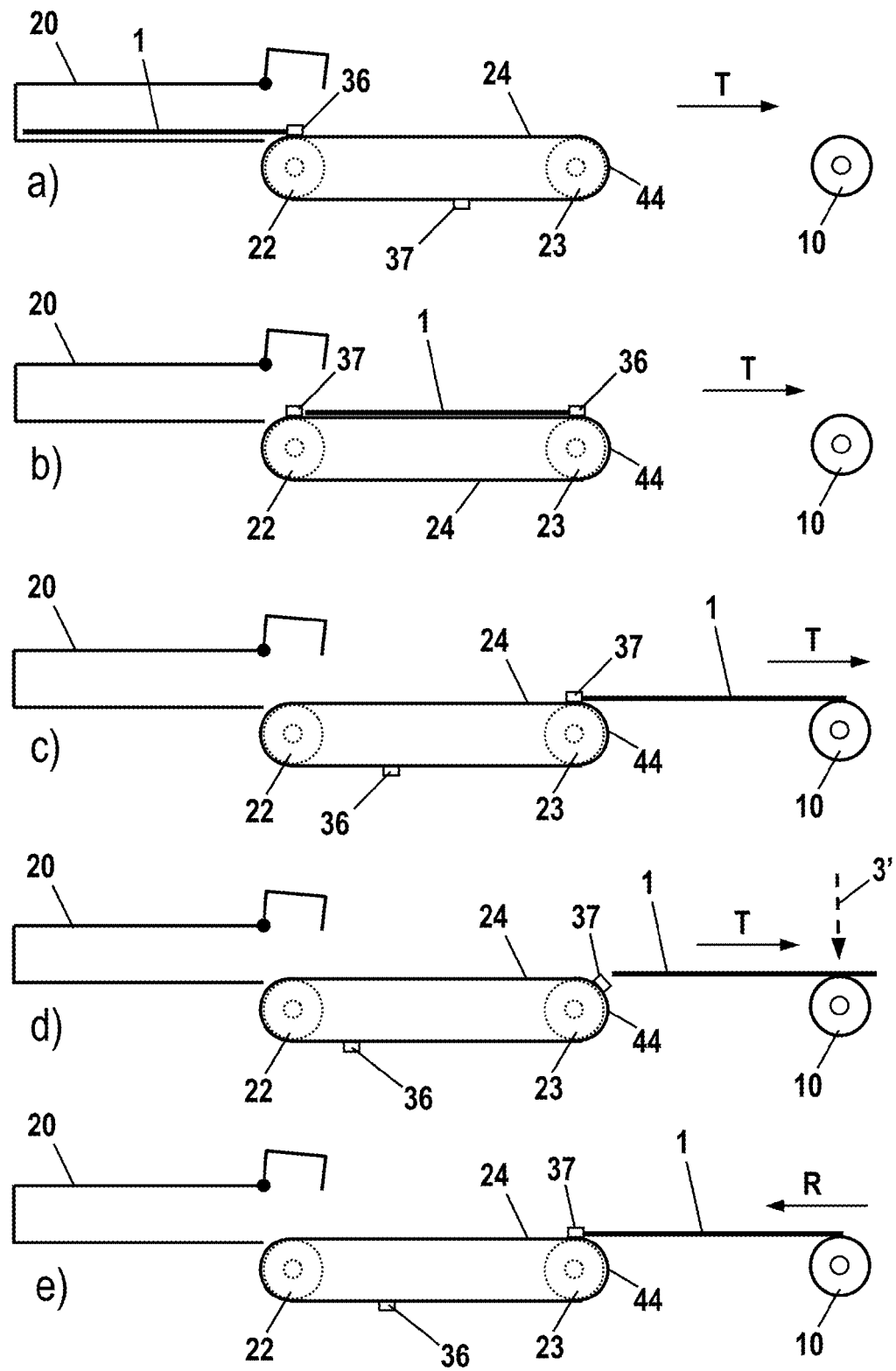
FIG. 6 a schematic representation of the removal of a storage phosphor plate from a cassette in a fifth preferred embodiment.

FIG. 6 shows a schematic representation of the removal of a storage phosphor plate 1 from a cassette 20 in a fifth preferred embodiment of the invention. In the preferred embodiment shown, a first removal element 36 is attached to a belt that is guided via two guide rollers 22 and 23. Through the rotation of the guide rollers 22 and 23, of which at least one can be put into rotation via a suitable drive, the relative position of the first removal element 36 with respect to the cassette 20 or the storage phosphor plate 1 that is located in the cassette 20 is changed.

Furthermore, the belt 24 is provided with a second removal element 37 whose distance to the first removal element 36 along the belt 24 is preferably slightly larger or equal to the length of the storage phosphor plate 1 that is to be removed from the cassette 20. A roller 10, by which the storage phosphor plate 1 can be transported past a read-out device, is disposed spaced apart, in the transport direction T, from the two guide rollers 22 and 23.

In the phase of the removal displayed in part a) of FIG. 6, the first removal element 36 was placed in a position, by rotation of the guide rollers 22 and 23 and a corresponding displacement of the belt 24, in which the removal element comes into contact with the front end of the storage phosphor plate 1. The first removal element 36, as was already explained in the context of the preferred embodiments shown in FIGS. 2 and 3, can be a magnet and/or a mechanical coupling element, for example a mechanical gripper or hook. Preferably, the first removal element 36 comprises one or more permanent magnets that are attached to the belt 24. In the shown position, the first removal element is coupled via magnetic forces or positive locking and/or force-fitted, respectively, with the storage phosphor plate 1.

Through a right hand rotation of the guide rollers 22 and 23, the first removal element 36, which is located on the belt 24, as well as the storage phosphor plate 1 that is coupled to the removal element is conveyed out of the cassette 20 in the transport direction T.

In part a) of FIG. 6, a phase is displayed in which the storage phosphor plate 1 has been completely removed from the cassette 20 and is supported on the upper side of the belt 24. The front end of the storage phosphor plate 1 is still coupled to the first removal element. Since the distance of the second removal element 37 from the first removal element 36 is only slightly larger than the length of the storage phosphor plate 1, the second removal element is now close to the rear end of the storage phosphor plate 1.

The first removal element 36 follows the curved path around the guide roller 23 as a result of the continuing rotation of the guide rollers 23 and 24 until the coupling with the storage phosphor plate 1 finally releases automatically, as has already been described in detail in the context of the examples in FIGS. 2 and 3.

In the case of a further continuation of the rotational movement of the guide rollers 22 and 23, the storage phosphor plate 1 is conveyed further by its rear end via the second removal element 37 in the transport direction T, meaning it is pushed. This phase is shown in part c) of FIG. 6 at a point in time at which the storage phosphor plate 1, which is pushed by the second removal element 37, already positions itself with its front end on the roller 10 that is located beneath the read-out device.

In the case of a continued rotation of the guide rollers 22 and 23, the second removal element, which is disposed on the belt 24, likewise follows the substantially circularly curved path 44 along the outer circumference of the guide roller 23, so that the second removal element 37 "dives away" downward, leaving the storage phosphor plate 1 now completely decoupled from the removal device and only being transported by the roller 10 in the transport direction T past the deflected stimulation light beam 3' of the read-out device.

After reading out the X-ray information stored in the storage phosphor plate 1, roller 10 conveys the storage phosphor plate again, in the reverse transport direction R, to the second removal element 37 which in the meantime has been moved into a position where the removal element can come into contact with the rear end of the storage phosphor plate 1.

The second removal element 37 has, corresponding to the first removal element 36, permanently magnetic elements and/or mechanical coupling elements, such as for example a gripper or hook, by which the removal element can couple to the storage phosphor plate 1 and can, in the case of a corresponding rotation of the guide rollers 22 and 23 in the reverse rotation direction, meaning to the left, convey the storage phosphor plate 1 in the return transport direction R again in the direction of the cassette 20. In this case, the return transport of the storage phosphor plate 1 into the cassette 20 takes place according to the previously described sequence in reversed order.

With the preferred embodiments described previously on the basis of FIGS. 2 to 6, the return of the storage phosphor plate 1 into the cassette 20 takes place substantially in the reversed order of the one used for the removal of the storage phosphor plate. In general, no additional, in particular mechanical, means or measures are hereby necessary to assure an automatic and reliable decoupling of the storage phosphor plate 1 from the respective removal element 30 to 37.

In order to support the automatic decoupling or to even improve its reliability, respectively, without increasing the effort device-wise at the same time, it is possible, additionally, to utilize the inertia of the storage phosphor plate 1. This can preferably be carried out in two different ways.

In a first variation, the removal elements 30 to 37, which have transported the storage phosphor plate 1 back into the cassette 20, are accelerated after the storage phosphor plate 1 has been placed in the cassette 20. The acceleration is thereby preferably high enough that the magnetic connection between the storage phosphor plate 1 and the respective removal element 30 to 37 breaks off.

In a second variation, the storage phosphor plate 1 is moved very quickly during its return transport into the cassette 20, wherein the removal elements 30 to 37 come to a rest suddenly prior to reaching the end position, in which the storage phosphor plate 1 is located completely in the cassette 20. The magnetic engagement with the removal element 30 to 37 is released due to the moving mass of the storage phosphor plate 1, so that the storage phosphor plate 1 is separated from the removal element 30 to 37 that is guiding the return.

These measures likewise contribute to a particularly reliable removal and/or return of the storage phosphor plate 1 from and into, respectively, the initial position, in particular the cassette 20, with a straightforward configuration at the same time.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. An apparatus for reading out X-ray information stored in a storage phosphor plate, the apparatus comprising:
   a receiving device configured to receive a storage phosphor plate;
   a removal device configured to remove the storage phosphor plate from the receiving device; and
   a read-out device configured to irradiate the storage phosphor plate, which has been removed from the receiving device, with stimulating light and to detect emission light which is stimulated in the storage phosphor plate; wherein
   the removal device includes at least one removal element configured to be coupled to the storage phosphor plate and moved along a curved path.

2. The apparatus according to claim 1, wherein the at least one removal element is configured to be coupled to the storage phosphor plate at a first position along the curved path, the storage phosphor plate is removed at least partially from the receiving device during a movement of the at least one removal element from the first position to a second position along the curved path, and the at least one removal element is configured to be decoupled from the storage phosphor plate during a movement of the at least one removal element beyond the second position along the curved path.

3. The apparatus according to claim 2, wherein the at least one removal element is configured to be automatically coupled to the storage phosphor plate at the first position along the curved path, and/or configured to be automatically decoupled from the storage phosphor plate during the movement beyond the second position along the curved path.

4. The apparatus according to claim 1, wherein the at least one removal element is configured to be coupled and/or decoupled to and from the storage phosphor plate, respectively, solely due to a movement by the at least one removal element along the curved path.

5. The apparatus according to claim 1, wherein the at least one removal element includes a magnetic element by which the at least one removal element is coupled to the storage phosphor plate.

6. The apparatus according to claim 1, wherein the at least one removal element is disposed on a connecting rod.

7. The apparatus according to claim 1, wherein the at least one removal element is disposed on a rotatable pulley or a rotatable roller.

8. The apparatus according to claim 1, wherein the at least one removal element is disposed on a belt that is guided across at least one curved guide.

9. The apparatus according to claim 1, wherein a plane including the curved path of the at least one removal element is perpendicular or substantially perpendicular to a plane including the storage phosphor plate.

10. The apparatus according to claim 1, wherein at least one section of the curved path is ellipse-shaped or substantially ellipse-shaped.

11. The apparatus according to claim 1, further comprising a transport device configured to transport the storage phosphor plate relative to the read-out device, wherein the removal device is configured to convey the storage phosphor plate toward the transport device and/or away from the transport device.

12. The apparatus according to claim 11, wherein the transport device includes at least one roller including at least one magnetic area.

13. The apparatus according to claim 1, wherein the removal device is configured to convey the storage phosphor plate into an interior of the apparatus.

14. The apparatus according to claim 1, wherein the removal device is configured to return the storage phosphor plate into the receiving device.

15. A system for reading out X-ray information stored in a storage phosphor plate, the system comprising a storage phosphor plate and an apparatus according to claim 1.

16. The system according to claim 15, wherein the storage phosphor plate is permanently magnetic and/or ferromagnetic at least in a partial region of the storage phosphor plate.

17. A method for reading out X-ray information stored in a storage phosphor plate, the method comprising the following steps of:

removing a storage phosphor plate from a receiving device;

reading out the storage phosphor plate, which has been removed from the receiving device, by irradiating the storage phosphor plate with stimulating light and detecting emission light stimulated in the storage phosphor plate; and during the removing step of the storage phosphor plate, moving at least one removal element along a curved path and coupling the at least one removal element to the storage phosphor plate.

* * * * *